United States Patent [19]

Homan

[11] Patent Number: 4,487,883

[45] Date of Patent: Dec. 11, 1984

[54] ONE-PART MOISTURE CURED AMINOSILOXANES

[75] Inventor: Gary R. Homan, Midland, Mich.

[73] Assignee: Dow Corning Corporation, Midland, Mich.

[21] Appl. No.: 534,845

[22] Filed: Sep. 22, 1983

Related U.S. Application Data

[63] Continuation-in-part of Ser. No. 453,638, Dec. 27, 1982, abandoned.

[51] Int. Cl.$^3$ .............................................. C08K 5/02
[52] U.S. Cl. ................................... 524/792; 525/370; 525/420; 525/437; 525/452; 528/17; 528/18; 528/19; 528/38
[58] Field of Search ............... 525/370, 420, 437, 452; 528/17, 18, 19, 38; 524/792

[56] References Cited

U.S. PATENT DOCUMENTS

| | | | |
|---|---|---|---|
| 3,832,203 | 8/1974 | Saunders et al. | 106/287 |
| 4,344,763 | 8/1982 | Tolgyesi et al. | 8/127.51 |
| 4,388,437 | 6/1983 | Ona | 524/588 |

FOREIGN PATENT DOCUMENTS 1112181 11/1981 Canada.
55-66506 8/1980 Japan.
2058103 4/1981 United Kingdom.

OTHER PUBLICATIONS

"New Types of Hair Setting Sprays Having Semi-Permanent Properties" by Fulvio Sardo, Amer. Cosmetics and Perfumery 87, 43–46, Dec. 1972.

*Primary Examiner*—Melvyn I. Marquis
*Attorney, Agent, or Firm*—James E. Bittell

[57] ABSTRACT

A composition consisting essentially of (A) a polymer having at least one nitrogen-hydrogen bond; and (B) a readily hydrolyzable, anhydrous additive selected from the group consisting of titanates, zirconates, vanadates, germanates, and mixtures thereof is disclosed. The uniqueness of this invention is that the polymer is crosslinked upon exposure to moisture, such as water vapor but is reverted to noncrosslinked polymer after exposure to liquid water. Furthermore, the components can be stored together, in the absence of moisture, with no gelation.

13 Claims, No Drawings

ONE-PART MOISTURE CURED AMINOSILOXANES

This application is a continuation-in-part of application Ser. No. 453,638, filed Dec. 27, 1982 now abandoned.

FIELD OF THE INVENTION

This invention relates to a composition, stable in the absence of moisture, consisting essentially of (A) a polymer having at least one nitrogen-hydrogen bond; and (B) a readily hydrolyzable, anhydrous additive selected from the group consisting of titanates, zirconates, vanadates, germanates and mixtures thereof. The uniqueness of this invention is that the polymer is crosslinked upon exposure to moisture such as water vapor, but is reverted to noncrosslinked polymer after exposure to liquid water. Furthermore, the components can be stored together, in the absence of moisture, with no gelation.

DESCRIPTION OF THE PRIOR ART

Polymers crosslinked upon exposure to moisture, but reverted to polymer after exposure to water, would find use in hair care applications, and reversible rubber or elastomer applications. In hair care applications, a composition would be applied to hair to serve as a hair set and conditioner. Upon washing, the composition would be reverted to polymer and act, again, as a hair conditioner. An object of this invention is to provide a composition capable of performing the above.

A composition described in the article entitled "New Types of Hair Setting Sprays having Semi-Permanent Properties" authored by Fulvia Sardo in Volume 87, *American Cosmetics and Perfumery*, pages 43–46 (December, 1972), discloses the use of alkyltitanates in combination with silanol endblocked dimethylpolysiloxanes as a hair set. This composition, however, has limited use, at best, as a hair conditioner and setting treatment. Furthermore, there is no mention of the composition's capability of reversion to its polymer.

Canadian Pat. No. 1,112,181 discloses a hair set composition consisting essentially of aminoalkylalkoxysilanes and a titanate ester. This composition also has limited use as a hair conditioner with no mention of reversion capabilities.

U.S. Pat. No. 3,832,203 discloses a composition for treating leather comprising an organic solvent solution of (A) a titanate or zirconate, a copolymer of trimethylsiloxane and $SiO_2$ units, a polysiloxane, and (B) an aminoalkyl substituted silane or siloxane. There is no mention of this composition being reversible and parts (A) and (B) cannot be stored together.

U.S. application for patent, Ser. No. 332,063, filed Dec. 18, 1981, now U.S. Pat. No. 4,388,437 discloses an organopolysiloxane composition, used for treating fibers, consisting essentially of an organopolysiloxane containing amine functionality, a surfactant, a titanate, zirconate or germanate, an organic acid, and water. The surfactant is needed to emulsify the siloxane. The acid is essential to adjust the pH to a desired range to control the rate of adsorption of the emulsion on the fiber. There is no mention of this composition's reversion capabilities.

An object of this invention is to provide a composition stable in the absence of moisture, but upon exposure to moisture, crosslinking occurs. A further object of this invention is to provide a composition crosslinked upon exposure to moisture, but reverted to polymer after exposure to water.

DETAILED DESCRIPTION

This invention relates to a composition, stable in the absence of moisture, consisting essentially of (A) a polymer having at least one nitrogen-hydrogen bond; and (B) a readily hydrolyzable, anhydrous additive selected from the group consisting of titanates, zirconates, vanadates, germanates and mixtures thereof. The uniqueness of this invention is that the polymer is crosslinked upon exposure to moisture such as water vapor, but is reverted to noncrosslinked polymer after exposure to liquid water. Furthermore, the components can be stored together in the absence of moisture with no gelation.

So far as is known at this time, any polymer containing at least one nitrogen-hydrogen bond can be employed for the purposes of this invention. Examples of suitable polymers include polyamides, polyesters, polyethers, polyurethanes, polyalkylenes such as polypropylene, polyethylene and polystyrene, and siloxanes. If the polymer is present in solid form, such as polystyrene, the polymer will have to be dissolved in a compatible solvent, such as toluene or xylene, so the additive can be mixed. Specific examples of suitable polymers include $$CH_3(C_2H_4)_2-N-\overset{H}{\underset{\overset{\|}{O}}{C}}-O(C_3H_6)_3CH_3,$$

$H_2NCH_2(CH_2COOCH_2)_3CH_3;$ $$\begin{array}{c} CH_3 \\ | \\ CH_3-[C-\!\!-\!\!-CH]_2CH_3 \\ | \quad | \\ CH_3 \ OCH_2CH_2NH_2 \end{array} \quad ;$$

$H_2NCH_2(CH_2-\underset{\overset{\|}{O}}{C}-OCH_2CH_2)_3CH_3;$ and $$CH_3(CH=CH)_6\underset{\overset{|}{NH_2}}{C}HCH_3,$$

which are examples of polyamides, polyesters, polyethers, polyurethanes, and polyalkylenes, respectively. A siloxane polymer is preferred however. Further preference is given to the siloxane polymer having the units containing the nitrogen-hydrogen bonds selected from the group consisting of

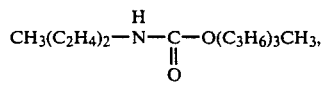

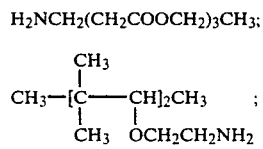

$O_{1.5}SiC_mH_{2m}NR_2'$, $O_{1.5}SiC_mH_{2m}NR'C_nH_{2n}NR_2'$,

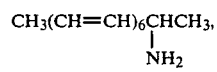

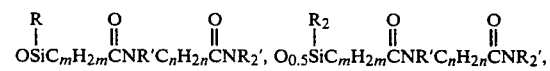

-continued

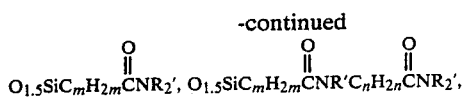

and mixtures thereof wherein R is selected from the group consisting of monovalent hydrocarbon radicals, substituted monovalent hydrocarbon radicals, hydrogen, and a radical having the general formula —OX, wherein X is selected from the group consisting of hydrogen, monovalent hydrocarbon radicals, and substituted monovalent hydrocarbon radicals; R' is selected from the group consisting of hydrogen, monovalent hydrocarbon radicals, and substituted monovalent hydrocarbon radicals; wherein at least one R' per siloxy unit is hydrogen; and m and n have values of 1 to 4.

It should be understood that the divalent radicals represented as $C_mH_{2m}$ and $C_nH_{2n}$ can be either linear or branched hydrocarbon radicals. Specific examples of suitable divalent hydrocarbon radicals represented by $C_mH_{2m}$ and $C_nH_{2n}$ in the above formula include —(CH$_2$)$_2$—, —(CH$_2$)$_3$—, —(CH$_2$)—, —CH$_2$CHCH$_3$CH$_2$— and

Specific examples of suitable monovalent hydrocarbon and substituted monovalent hydrocarbon radicals for R, R', and X are alkyl radicals such as the methyl, ethyl, propyl, butyl, amyl, cyclohexyl, decyl, dodecyl, and octadecyl radicals; alkenyl radicals such as the vinyl and allyl radicals; aryl radicals such as the phenyl and biphenyl radicals; alkaryl and aralkyl radicals such as the tolyl and benzyl radicals; and the corresponding substituted hydrocarbon radicals such as the chloropropyl, 3,3,3-trifluoropropyl, dichlorophenyl, cyanobutyl, and nitrophenyl radicals.

A siloxane polymer having the nitrogen-hydrogen bond units in the siloxy unit having the general formula

wherein R is a monovalent hydrocarbon radical, R' is hydrogen, m has a value of 3 or 4 and n has a value of 2 is preferred. R being an alkyl radical is further preferred with methyl being optimal. The composition of the other units in the siloxane polymer is not critical for the purpose of this invention. The other units of the siloxane polymer can be selected from the group consisting of $RSiO_{3/2}$, $R_2SiO$, and $R_3SiO_{\frac{1}{2}}$ units wherein R is as defined above. A siloxane polymer composed primarily of $R_2SiO$ units is preferred. Furthermore the endblocking and the structure of the polymer is not critical for the purpose of this invention as long as the siloxane polymer contains at least one nitrogen-hydrogen bond. Also, the siloxane polymer containing at least one nitrogen-hydrogen bond can be blended with other functional siloxanes or non-functional siloxanes, such as dimethylsiloxane or dimethylcyclosiloxane. However, a greater amount of amine or amide present leads to greater crosslinking.

A siloxane polymer having the general formula

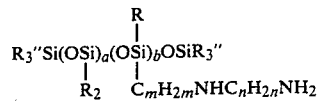

wherein R is as defined above, R" is selected from the group consisting of monovalent hydrocarbon radicals, substituted monovalent hydrocarbon radicals and a radical having the general formula —OX wherein X is selected from the group consisting of hydrogen, monovalent hydrocarbon radicals, and substituted monovalent hydrocarbon radicals, a+b has a value of 1 to 2000 with a having a value of 0 to 1999, and b having a value of 1 to 2000, is preferred. Specific examples of suitable monovalent hydrocarbon radicals and substituted monovalent hydrocarbon radicals for R" are as defined above for R, R', and X. But, further preference is given to R" being a monovalent hydrocarbon radical, with R" being an alkyl radical being further preferred, and methyl being optimal. The value of a+b having a value of 50 to 400 with a having a value of 49 to 399 and b having a value of 1 to 30 is also further preferred. A siloxane polymer selected from the group consisting of

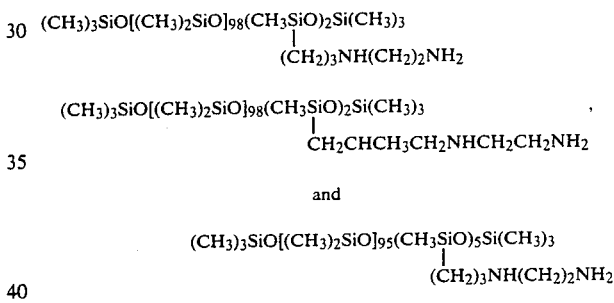

is further preferred.

So far as is known at this time, any readily hydrolyzable, anhydrous additive selected from the group consisting of titanates, zirconates, vanadates, germanates and mixtures thereof can be employed for the purpose of this invention. Specific examples of suitable organic zirconates include octyleneglycolzirconate, tetra-2-ethylhexylzirconate, tetraisopropylzirconate, tertiarybutyltrimethylzirconate and mixtures thereof. Specific examples of suitable organic titanates include tetraethyltitanate, tetradecyltitanate, tetra-2-ethylhexyltitanate, tetradodecyltitanate, tetraisopropyltitanate, tetrabutyltitanate and mixtures thereof. Specific examples of suitable organic germanates include tetraethylgermanate, tetraisopropylgermanate, and tetradecylgermanate. Specific examples of suitable organic vanadates include vanadium triisopropoxide oxide and vanadium tri-n-propoxide oxide.

Titanates are preferred, however. Organic titanates selected from the group consisting of alkyl titanates and titanium chelates are further preferred. Alkyl titanates have the general formula $Ti(OD)_4$ wherein D is a monovalent hydrocarbon radical or a substituted monovalent hydrocarbon radical.

Titanium chelates have the general formulae

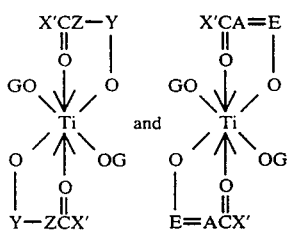 and 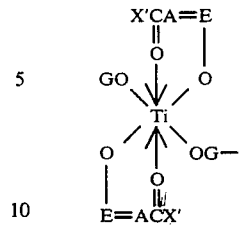

wherein G is a monovalent hydrocarbon or substituted monovalent hydrocarbon radical, X' is selected from the group consisting of hydrogen, —OCH$_2$CH$_3$, —OH, monovalent hydrocarbon radicals, and substituted monovalent hydrocarbon radicals, Z and Y are divalent hydrocarbon or substituted divalent hydrocarbon radicals, and A and E are trivalent or substituted trivalent hydrocarbon radicals.

Specific examples of suitable monovalent hydrocarbon or substituted monovalent hydrocarbon radicals for D, X', and G are alkyl radicals such as the methyl, ethyl, propyl, butyl, amyl, cyclohexyl, decyl, dodecyl, and octadecyl radicals; alkenyl radicals such as the vinyl and allyl radicals; aryl radicals such as the phenyl and biphenyl radicals; alkaryl and aralkyl radicals such as the tolyl and benzyl radicals; and the corresponding substituted hydrocarbon radicals such as the chloropropyl, 3,3,3-trifluoropropyl, dichlorophenyl, cyanobutyl, and nitrophenyl radicals.

The hydrocarbon and substituted hydrocarbon radicals for Y and Z are divalent radicals. Though the above examples of suitable hydrocarbon and substituted hydrocarbon radicals for D, X' and G are in monovalent form, similar divalent radicals are suitable for Y and Z. Specific examples of suitable divalent hydrocarbon radicals include

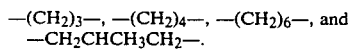

The hydrocarbon and substituted hydrocarbon radicals for A and E are trivalent radicals. Though the above examples of suitable hydrocarbon and substituted hydrocarbon radicals for D, X', and G are in monovalent form, similar trivalent radicals are suitable for A and E. Specific examples of suitable trivalent hydrocarbon radicals include

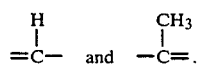

Specific examples of suitable titanates having the general formula Ti(OD)$_4$ include tetraisopropyltitanate, tetra-n-butyltitanate, and tetrakis(2-ethylhexyl)titanate. Specific examples of suitable titanate having the general formula include titanium acetylacetonate and titanium ethyl acetylacetonate.

Titanates having the general formula Ti(OD)$_4$ wherein D is an alkyl radical are preferred. Further preference is given to the titanate having the general formula Ti(OD)$_4$ wherein D is selected from the group consisting of isopropyl, 2-ethylhexyl, and n-butyl radicals.

If desired the composition may also contain an anhydrous organic solvent. Examples of suitable solvents include aliphatic hydrocarbon and aliphatic halogenated hydrocarbon solvents such as hexane, heptane, and 1,1,1-trichloroethane; and aromatic hydrocarbon solvents such as toluene and xylene. The solvent, 1,1,1-trichloroethane, is preferred.

Compositions containing 0.97 to 90 percent by weight of the siloxane, 0.03 to 15 percent by weight of the metallic additive, and 1 to 99 percent by weight of a solvent are preferred. Compositions containing from 3 to 20 percent by weight of the siloxane, 0.1 to 3 percent by weight of the metallic additive and 77 to 96.9 percent by weight of a solvent are further preferred.

If desired, the composition may also contain 0.01 to 50 percent by weight of an alkoxy silane having at least two alkoxy groups per silicon for added durability. Specific examples of suitable alkoxy silanes include methyl trimethoxysilane and a silane having the general formula NH$_2$CH$_2$CH$_2$NHCH$_2$CH$_2$CH$_2$Si(OCH$_3$)$_3$.

In addition to the essential ingredients, the composition of this invention may include minor quantities of optional materials which are added for specific purposes. Such other ingredients include, but are not limited to, medicaments such as anti-dandruff compounds, solvents, perfumes, sequestering agents, conditioning agents such as quaternary ammonium compounds, thickening agents, fillers, opacifiers, anti-static agents, and antimicrobial preservatives, of which silicone is one.

The method of preparation of the components of the present invention are well known to those skilled in the art and detailed elsewhere in the literature. Hence no time or space need be devoted here to a repetition of such information. As far as is known at this time, the order or method of mixing the components employed is not critical for the purpose of this invention.

Suitable uses for this composition are in the field of hair care and anywhere there is need for a reversible rubber or elastomer. In the field of hair care, preference is given to applying the composition to preset and dried hair. The composition can be applied to the hair in any suitable form such as in thickened form by hand, in viscous form, by aerosol, or by pump spray. The composition after curing on the hair acts to hold any set in the hair even when exposed to atmospheric humidity, but when the hair is contacted directly with water such as by washing, the set is removed from the hair. Washing hair with a shampoo rather than just water is even more effective in removing the set from the hair. However, sufficient composition remains on the hair to act as a conditioner for the wet hair. Furthermore, if the hair is reset and dried, the composition again acts to hold the set in the hair although to a somewhat lesser extent than after the initial application of the composition. Although not intending to be bound by this theory, applicant believes that the cured composition when contacted directly with water such as by washing, reverts to the noncrosslinked, uncured polysiloxane which acts as the conditioner for the wet hair. When the hair is again dried however, applicant believes that the composition that remains on the hair again cures to sufficient extent to improve the set holding properties of the hair. The term "hair" as used in the present invention includes treated and untreated human hair, animal hair, and any type of fiber that needs gloss, ease of combing, set hold, feel of fullness, protection from the elements such as sun, and reduced fly-away. Treated hair includes hair that is chemically changed and/or damaged by permanents and dyes. Setting hair means to curl, wave, control, or straighten hair.

Now in order that those skilled in the art may better understand how the present invention can be practiced, the following examples are given by way of illustration and not by way of limitation. All parts and percents referred to herein are by weight unless otherwise specified.

EXAMPLE 1

The following formulations were prepared by weighing the components into a 4 oz. bottle, capping, and shaking:

Formulation A
10 grams $(CH_3)_3SiO[(CH_3)_2SiO]_{98}(CH_3SiO)_2Si(CH_3)_3$
                               |
                               $(CH_2)_3NH(CH_2)_2NH_2$ 0.5 grams tetraisopropyltitanate

Formulation B
100 grams $(CH_3)_3SiO[(CH_3)_2SiO]_{98}(CH_3SiO)_2Si(CH_3)_3$
                                |
                                $(CH_2)_3NH(CH_2)_2NH_2$ 7.5 grams tetraisopropyltitanate

Formulation C
100 grams $(CH_3)_3SiO[(CH_3)_2SiO]_{98}(CH_3SiO)_2Si(CH_3)_3$
                                |
                                $(CH_2)_3NH(CH_2)_2NH_2$ 7.5 grams tetrakis(2-ethylhexyl)titanate

Formulation D
100 grams $(CH_3)_3SiO[(CH_3)_2SiO]_{95}(CH_3SiO)_5Si(CH_3)_3$
                                |
                                $(CH_2)_3NH(CH_2)_2NH_2$ 7.5 grams tetraisopropyltitanate

Formulation E
90 percent by weight
$(CH_3)_3SiO[(CH_3)_2SiO]_{98}(CH_3SiO)_2Si(CH_3)_3$
           |
           $CH_2CHCH_3CH_2NHCH_2CH_2NH_2$ 10 percent by weight tetraisopropyltitanate

Formulation F
90 percent by weight
$(CH_3)_3SiO[(CH_3)_2SiO]_{98}(CH_3SiO)_2Si(CH_3)_3$
           |
           $CH_2CHCH_3CH_2NHCH_2CH_2NH_2$ 10 percent by weight tetra-n-butyltitanate

Formulation G
90 percent by weight
$(CH_3)_3SiO[(CH_3)_2SiO]_{98}(CH_3SiO)_2Si(CH_3)_3$
           |
           $CH_2CHCH_3CH_2NHCH_2CH_2NH_2$ 10 percent by weight tetrakis(2-ethylhexyl)titanate

Formulation H
90 percent by weight
$(CH_3)_3SiO[(CH_3)_2SiO]_{98}(CH_3SiO)_2Si(CH_3)_3$
           |
           $CH_2CHCH_3CH_2NHCH_2CH_2NH_2$ 10 percent by weight titanium acetylacetonate

Formulation I
90 percent by weight
$(CH_3)_3SiO[(CH_3)_2SiO]_{98}(CH_3SiO)_2Si(CH_3)_3$
           |
           $CH_2CHCH_3CH_2NHCH_2CH_2NH_2$ 10 percent by weight titanium ethyl acetylacetonate

Formulation J
10 grams $(CH_3)_3SiO[(CH_3)_2SiO]_{98}(CH_3SiO)_2(CH_3)_3$
                               |
                               $(CH_2)_3N(CH_3)_2$ 0.5 grams tetraisopropyltitanate

Formulation K
10 grams $(CH_3)_3SiO[(CH_3)_2SiO]_{98}(CH_3SiO)_2Si(CH_3)_3$
                               |
                               $(CH_2)_3NH(CH_2)_2NH_2$ 0.5 grams tetraoctylene glycol titanium chelate

Formulation L
10 grams $(CH_3)_3SiO[(CH_3)_2SiO]_{98}(CH_3SiO)_2Si(CH_3)_3$
                               |
                               $(CH_2)_3N(CH_2)_2NH_2$ 0.75 grams triethanolamine titanium chelate

Formulation M
90 percent by weight
$(CH_3)_3SiO[(CH_3)_2SiO]_{98}(CH_3SiO)_2Si(CH_3)_3$
           |
           $CH_2CHCH_3CH_2NHCH_2CH_2NH_2$ 10 percent by weight tetraoctylene glycol titanium chelate

Formulation N
90 percent by weight
$(CH_3)_3SiO[(CH_3)_2SiO]_{98}(CH_3SiO)_2Si(CH_3)_3$
           |
           $CH_2CHCH_3CH_2NHCH_2CH_2NH_2$ 10 percent by weight triethanolamine titanium chelate After mixing, the fluids were clear and colorless and there were no apparent increases in viscosity. The caps were removed and a portion of the fluid poured into aluminum cups exposed to atmospheric air. The results are as follows:

| Formulation | Surface Skin Time, 23° C. | Tack Free Time, 23° C. |
| --- | --- | --- |
| A | 3 secs | 12 secs |
| B | immedate | immedate |
| C | 10 secs | 2 min |
| D | 2 secs | 10 secs |

| Formulation | Surface Skin Time, 23° C. | Tack Free Time, 23° C. |
| --- | --- | --- |
| E | 1 sec | 1 sec |
| F | 1 sec | 20 sec |
| G | 5 min | 21 min |
| H | 12 secs | 4.5 min |
| I | 45 secs | 4 min |
| J* | none | — |
| K* | none | — |
| L* | none | — |
| M* | none | — |
| N* | none | — |

*Included for purposes of comparison

After 24 hours of exposure, formulations A, B, C, D, E, F, G, H, and I were cured to a thickness of about 1/16 inch while the materials kept in the capped bottles were still unchanged.

Formulation J indicates the importance of the N—H bond. The composition was exposed to air for 24 hours and showed no surface skin.

Formulations, K, L, M, and N indicate the importance of the titanate being readily hydrolyzable. The tetraoctylene glycol titanium chelate and the triethanolamine titanium chelate used in the formulations are not readily hydrolyzable. These formulations were also exposed to air for 24 hours and showed no evidence of forming a surface skin. The absence of surface skin in these formulations after 24 hours of exposure to the atmosphere is a simple test that can be employed to distinguish organic titanates, zirconates, germanates, and vanadates that are not readily hydrolyzable.

Formulation D was shelf-aged for 16 days and then the above process was repeated giving similar results. A portion of its cured rubber, 1/16 inch thick, was also heat aged 3 days at 100° C. with no apparent adverse effects. Another portion of this cured rubber was immersed in tap water and became soft after 3 hours. After 3 days of immersion, the cured rubber reverted to the polymer and a white precipitate.

EXAMPLE 2

A formulation was evaluated for the ability of the present invention to hold a set to hair. The formulation consisted of 10 percent by weight of

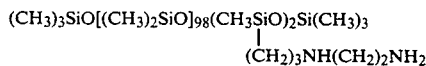

$(CH_3)_3SiO[(CH_3)_2SiO]_{98}(CH_3SiO)_2Si(CH_3)_3$
|
$(CH_2)_3NH(CH_2)_2NH_2$ 1 percent by weight of tetraisopropyltitanate, and 89 percent by weight of 1,1,1-trichloroethane. The components were mixed together and the formulation was then placed in an aerosol can with 50 cc of dichlorodifluoromethane propellant.

The test consisted of spraying the formulation onto undyed, preset, and dried hair and then exposing the hair to a water mist. An untreated specimen, also undyed, preset, and dried, was also exposed to the water mist.

The silicone treated hair held its set while the control completely lost its set after 24 hours exposure to atmospheric air.

EXAMPLE 3

The following formulations were prepared by weighing the components into a 1 ounce bottle, capping and shaking. The siloxane employed in the formulations had the general formula of

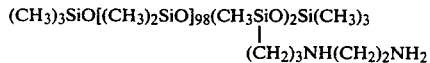

$(CH_3)_3SiO[(CH_3)_2SiO]_{98}(CH_3SiO)_2Si(CH_3)_3$
|
$(CH_2)_3NH(CH_2)_2NH_2$

Nine grams of the siloxane and 1 gram of the additive was employed. Vanadium triisopropoxide oxide, zirconium-n-propoxide, and germanium butoxide were the additives employed in Formulations A, B, and C, respectively.

After mixing, the formulations were clear with no apparent increase in viscosity. The caps were then removed and a portion poured into aluminum cups exposed to atmospheric moisture. The results are as follows:

| Formulation | Surface Skin Time, 23° C. | Tack Free Time, 23° C. |
| --- | --- | --- |
| A | 2 seconds | 5 seconds |
| B | 15 seconds | 85 seconds |
| C | 3 seconds | 20 seconds |

After 24 hours of exposure, formulations A, B, and C were cured to a thickness of about 1/16 inch while the material kept in the capped bottles were still in an unchanged, fluid state.

That which is claimed:

1. A composition, stable in the absence of moisture, consisting essentially of (A) a siloxane polymer having at least one unit containing a nitrogen-hydrogen bond selected from the group consisting of

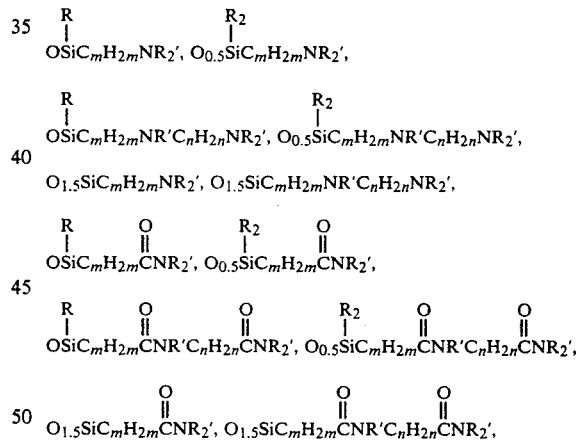

and mixtures thereof wherein R is selected from the group consisting of monovalent hydrocarbon radicals, substituted monovalent hydrocarbon radicals, and a radical having the general formula —OX wherein X is selected from the group consisting of monovalent hydrocarbon radicals and substituted monovalent hydrocarbon radicals; R' is selected from the group consisting of hydrogen, monovalent hydrocarbon radicals, and substituted monovalent hydrocarbon radicals; wherein at least one R' per siloxy unit is hydrogen; and m and n have values of 1 to 4 and the other units of the siloxane polymer are selected from the group consisting of RSiO$_{3/2}$, R$_2$SiO, and R$_3$SiO$_{\frac{1}{2}}$ wherein R is as defined above, and (B) a readily hydrolyzable, anhydrous additive selected from the group consisting of titanates, zirconates, vanadates, germanates and mixtures thereof.

2. A composition as defined in claim 1 wherein R is a monovalent hydrocarbon radical.

3. A composition as defined in claim 2 wherein (B) the anhydrous additive is a titanate.

4. A composition as defined in claim 3 wherein the units containing the nitrogen-hydrogen bond in (A) the siloxane polymer are $$\overset{R}{\underset{|}{OSiC_mH_{2m}NR'C_nH_{2n}NR_2'}}$$

wherein R is a monovalent hydrocarbon radical, R' is hydrogen, m has a value of 3 or 4, and n has a value of 2; and (B) the titanate is an alkyl titanate having the general formula Ti(OD)$_4$ wherein D is an alkyl radical.

5. A composition as defined in claim 4 wherein (A) the siloxane polymer has the general formula $$\underset{R_2 \quad C_mH_{2m}NHC_nH_{2n}NH_2}{\overset{R}{\underset{|}{R_3''Si(OSi)_a(OSi)_bOSiR_3''}}}$$

wherein R is an alkyl radical, R" is a monovalent hydrocarbon radical, and a+b has a value of 1 to 2,000 with a having a value of 0 to 1,999 and b having a value of 1 to 2,000.

6. A composition as defined in claim 5 wherein R" is an alkyl radical.

7. A composition as defined in claim 6 wherein R and R" are methyl radicals, a+b has a value of 50 to 400 with a having a value of 49 to 399 and b having a value of 1 to 30.

8. A composition as defined in claim 7 wherein (A) the siloxane polymer is selected from the group consisting of $$\underset{(CH_2)_3NH(CH_2)_2NH_2}{\overset{|}{(CH_3)_3SiO[(CH_3)_2SiO]_{98}(CH_3SiO)_2Si(CH_3)_3}}$$

$$\underset{CH_2CHCH_3CH_2NHCH_2CH_2NH_2}{\overset{|}{(CH_3)_3SiO[(CH_3)_2SiO]_{98}(CH_3SiO)_2Si(CH_3)_3}}$$

and $$\underset{(CH_2)_3NH(CH_2)_2NH_2}{\overset{|}{(CH_3)_3SiO[(CH_3)_2SiO]_{95}(CH_3SiO)_5Si(CH_3)_3}}$$

and in (B) D is selected from the group consisting of isopropyl, 2-ethylhexyl, and n-butyl radicals.

9. A composition as defined in claim 8 wherein the composition contains (C) an anhydrous organic solvent for components (A) and (B).

10. A composition as defined in claim 9 wherein (C) the solvent is 1,1,1 trichloroethane.

11. A composition as defined in claim 10 wherein the composition consists essentially of 0.97 to 90 percent by weight of Component (A), 0.03 to 15 percent by weight of Component (B), and 1 to 99 percent by weight of Component (C).

12. A composition as defined in claim 11 wherein the composition consists essentially of 3 to 20 percent by weight of Component (A), 0.1 to 3 percent by weight of Component (B), and 77 to 96.9 percent by weight of Component (C).

13. A composition as defined in claim 12 wherein the composition contains 0.01 to 50 percent by weight of an alkoxy silane having at least two alkoxy groups per silicon.

* * * * *

UNITED STATES PATENT AND TRADEMARK OFFICE
CERTIFICATE OF CORRECTION

PATENT NO. : 4,487,883
DATED : December 11, 1984
INVENTOR(S) : Gary R. Homan

It is certified that error appears in the above-identified patent and that said Letters Patent is hereby corrected as shown below:

In Column 8, line 40, "$(CH_2)_3N(CH_2)_2NH_2$" should read -- $(CH_2)_3NH(CH_2)_2NH_2$ --.

In Column 8, line 66, "immedate" should read -- immediate --.

Signed and Sealed this

Seventh Day of May 1985

[SEAL]

Attest:

DONALD J. QUIGG

*Attesting Officer*   *Acting Commissioner of Patents and Trademarks*